(12) United States Patent
Arányi et al.

(10) Patent No.: US 7,176,213 B2
(45) Date of Patent: Feb. 13, 2007

(54) IMIDAZOQUINOLINE DERIVATIVES AND THEIR USE AS ADENOSINE A3 LIGANDS

(75) Inventors: Péter Arányi, Budapest (HU); László Balázs, Göd (HU); Mária Balogh, Dunakeszi (HU); Sándor Bátori, Budapest (HU); Kinga Boér, Budapest (HU); Katalin Gerber, Budapest (HU); Zoltán Kapui, Budapest (HU); Endre Mikus, Budapest (HU); Geza Tímári, Vecsés (HU); T. Nagy Lajos, Budapest (HU); Katalin Urbán-Szabó, Budapest (HU); Judit Vargáné Szeredi, Budapest (HU)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/499,251

(22) PCT Filed: Dec. 17, 2002

(86) PCT No.: PCT/HU02/00144

§ 371 (c)(1),
(2), (4) Date: Nov. 22, 2004

(87) PCT Pub. No.: WO03/053969

PCT Pub. Date: Jul. 3, 2003

(65) Prior Publication Data

US 2005/0070566 A1    Mar. 31, 2005

(30) Foreign Application Priority Data

Dec. 21, 2001    (HU) ..................... 0105406

(51) Int. Cl.
*A01N 43/42* (2006.01)
*A61K 31/44* (2006.01)
*C07D 471/00* (2006.01)
*C07D 491/00* (2006.01)
*C07D 498/00* (2006.01)

(52) U.S. Cl. .................. 514/292; 546/84
(58) Field of Classification Search .......... 514/232.5, 514/253.03, 292; 544/125, 361; 546/84
See application file for complete search history.

(56) References Cited

U.S. PATENT DOCUMENTS

| 4,075,343 A | 2/1978 | Kadin |
| 4,279,912 A | 7/1981 | Ager et al. |
| 4,333,934 A | 6/1982 | Barnes et al. |
| 4,387,098 A | 6/1983 | Barnes et al. |
| 2005/0234056 A1* | 10/2005 | Aranyi et al. ............ 514/232.5 |

FOREIGN PATENT DOCUMENTS

EP    0062580    10/1982

OTHER PUBLICATIONS

Tilley et al., "Adenosine and inosine increase cutaneous vasopermeability by activating A3 receptors on mast cells", The journal of clinical investigation, 2000, vol. 105, pp. 361-367.*
Shneyvays et al., "Insights into adenosine A1 and A3 receptors function: cardiotoxicity and cardioprotection", Drug development research, vol. 50, pp. 324-337.*
Ager, Ian R. et al., J. Med. Chem., vol. 31(6), pp. 1098-1115 (1988).
Clements-Jewery, Stephen et al., J. Med. Chem., vol. 31(6), pp. 1220-1226 (1988).

* cited by examiner

Primary Examiner—Margaret D. Seaman
Assistant Examiner—Niloofar Rahmani
(74) Attorney, Agent, or Firm—Michael D. Alexander; Jiang Lin (57) ABSTRACT

The present invention relates to adenosine $A_3$ receptor ligands of the general formula (I), within those preferably antagonists, as well as their salts, solvates and isomers, and the pharmaceutical compositions containings them, to the use of the compounds of the general formula (I), as well as their salts, solvates and isomers, to the preparation of the compounds of the general formula (I) and their salts, solvates and isomers, furthermore to the new intermediates of the general formulae (II) and (III) and to the preparation thereof.

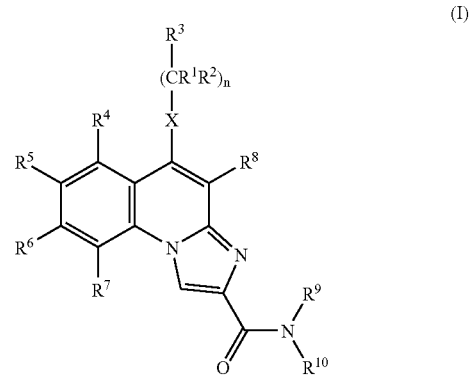

25 Claims, 2 Drawing Sheets

III.
Fig. 3

VII.
Fig. 7

VIII.
Fig. 8

Reaction scheme 1

Fig.9

IMIDAZOQUINOLINE DERIVATIVES AND THEIR USE AS ADENOSINE A3 LIGANDS

The present invention relates to adenosine $A_3$ receptor ligands of the general formula (I), within those preferably antagonists, as well as their salts, solvates and isomers, and the pharmaceutical compositions containing them, to the use of the compounds of the general formula (I), as well as their salts, solvates and isomers, to the preparation of the compounds of the general formula (I) and their salts, solvates and isomers, furthermore to the new intermediates of the general formulae (II) and (III) and to the preparation thereof.

Adenosine is a well-known component of several endogenous molecules (ATP, $NAD^+$, nucleic acids). Besides, it plays an important regulatory role in many physiological processes. The effect of adenosine on heart function was discovered already in 1929. (Drury and Szentgyörgyi, J Physiol 68:213, 1929). The identification of an increasing number of physiological functions mediated by adenosine and the discovery of new adenosine receptor subtypes give possibilities for therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for inhibiting the adenylate cyclase by coupling to $G_i$ membrane protein, partly influences other second messenger systems. The $A_2$ receptor subtype can be subdivided into two further subtypes—$A_{2a}$ and $A_{2b}$—, which receptors stimulate the adenylate cyclase activity. The sequence of adenosine $A_3$ receptors has been recently identified from rat testis cDNA library. Later it was proved that it corresponds to a novel, functional adenosine receptor. The activation of the $A_3$ receptors is connected also with several second-messenger systems: e.g. inhibiting of adenylate cyclase, and stimulating of phospholipase C and D.

The adenosine receptors are found in several organs and regulate their functions. Both $A_1$ and $A_{2a}$ receptors play important roles in the central nervous system and cardiovascular system. In the CNS, the adenosine inhibits the release of synaptic transmitters which effect is mediated by $A_1$ receptors. In the heart, also the $A_1$ receptors mediate the negative inotropic, chronotropic and dromotropic effects of adenosine. The adenosine $A_{2a}$ receptors located relatively in a higher amount in the striatum, display a functional interaction with dopamine receptors in regulating the synaptic transmission. The $A_{2a}$ adenosine receptors on endothelial and smooth muscle cells are responsible for adenosine-induced vasodilation.

On the basis of mRNA identification, the $A_{2b}$ adenosine receptors are widely distributed in different tissues. They have been identified almost in every cell type but its expression is the highest in the intestine and the bladder. This subtype probably also has important regulatory function in the regulation of the vascular tone and plays a role in the function of mast cells.

Contrary to $A_1$ and $A_{2a}$ receptors, where the tissue distribution was detected on the protein level, the presence of $A_{2b}$ and $A_3$ receptors was detected on the basis of their mRNA level. Expression levels for $A_3$ adenosine receptors are rather low comparing to other subtypes and highly species dependent. $A_3$ adenosine receptors are expressed primarily in the central nervous system, testis, immune system and appear to be involved in the modulation of mediator release from mast cells in immediate hypersensitivity reaction.

The $A_3$ antagonists published so far in the literature belong to the groups of flavonoides, 1,4-dihydropyridine derivatives, triazoloquinazolines, thiazolonaphthyridines and thiazolopyrimidines. The present invention relates to a novel type of effective $A_3$ antagonists, which have the imidazoquinlolin structure.

For therapeutic use it is essential to ensure that the molecule does not bind, or bind only in the case of very high concentration to the $A_1$, $A_{2a}$ and $A_{2b}$ sub-types of the adenosine receptor. Our present invention relates to the compounds of the general formula (I) as well as their salts, solvates and isomers which have great selectivity for the $A_3$ sub-type of the adenosine receptor.

Our aim was to prepare $A_3$ ligands first of all with imidazoquinolin structure, and within those preferably antagonists, which have strong antagonistic effect and show high selectivity for the $A_3$ receptor, ie. they inhibit the $A_3$ receptor in much lower concentration than they inhibit the $A_1$, $A_{2a}$ and $A_{2b}$ receptors. Further aims were to have stability, bioavailability, therapeutic index and toxicity data which make possible to develope the new compounds into drug substances and that due to their favourable enteral absorbtion the compounds can be applied orally.

We have found that the compounds of the general formula (I)—wherein $R^1$ stands for hydrogen atom or a straight or branched $C_{1-4}$ alkyl group;

$R^2$ stands for hydrogen atom or a straight or branched $C_{1-4}$ alkyl group;

$R^3$ stands for hydrogen atom or a straight or branched $C_{1-4}$ alkyl group, or $C_{3-6}$ cycloalkyl group, or a phenyl group, thienyl group, or furyl group, optionally substituted by one or more straight or branched $C_{1-4}$ alkyl group, straight or branched $C_{1-4}$ alkoxy group, or halogen atom, or for a 5- or 6 membered heteroaromatic ring-containing one, two or three nitrogen atoms or a 5 membered heteroaromatic ring containing one nitrogen atom and one oxygen atom or one nitrogen atom and one sulphur atom, optionally substituted by one or more straight or branched $C_{1-4}$ alkyl group, straight or branched $C_{1-4}$ alkoxy group, or halogen atom;

$R^4$, $R^5$, $R^6$ and $R^7$ stand independently from each other for hydrogen atom, a straight or branched $C_{1-4}$ alkyl group, straight or branched $C_{1-4}$ alkoxy group, hydroxy group or halogen atom; or $R^4$ and $R^7$ stand for hydrogen atom and $R^5$ and $R^6$ form together a methylenedioxy group $R^8$ stands for hydrogen atom or a cyano group, aminocarbonyl group, $C_{1-4}$ alkoxycarbonyl group, or carboxy group;

$R^9$ and $R^{10}$ stand independently from each other for hydrogen atom or a straight or branched $C_{1-4}$ alkyl group, or a $C_{3-6}$ cycloalkyl group, or a phenyl group, phenyl-($C_{1-4}$) alkyl group, thienyl-($C_{1-4}$)alkyl group or furyl-($C_{1-4}$)alkyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for a 5 or 6 membered heteroaromatic ring, containing one, two or three nitrogen atoms, or a 5 membered heteroaromatic ring, containing one nitrogen atom and one oxygen atom or one nitrogen atom and one sulphur atom, optionally substituted by one or more straight or branched $C_{1-4}$ alkyl group, straight or branched $C_{1-4}$ alkoxy group, or halogen atom; or for a —$(CH_2)_m$—OH or —$(CH_2)_o$—$NR^{12}R^{13}$ group, or $R^9$ and $R^{10}$ form together with the nitrogen atom a 3–7 membered heterocyclic group, optionally substituted by a straight or branched $C_{1-4}$ alkyl group;

$R^{12}$ and $R^{13}$ stand independently from each other for hydrogen atom or a straight or branched $C_{1-4}$ alkyl group, or a $C_{3-6}$ cycloalkyl group, or a phenyl group, phenyl-$(C_{1-4})$ alkyl group, thienyl-$(C_{1-4})$alkyl group or furyl-$(C_{1-4})$alkyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for a 5 or 6 membered heteroaromatic ring, containing one, two or three nitrogen atoms, or a 5 membered heteroaromatic ring, containing one nitrogen atom and one oxygen atom or one nitrogen atom and one sulphur atom, optionally substituted by one or more straight or branched $C_{1-4}$ alkyl group, straight or branched $C_{1-4}$ alkoxy group, or halogen atom, or for a —$(CH_2)_m$—OH or —$(CH_2)_o$—$NR^{12}R^{13}$ group, or $R^{12}$ and $R^{13}$ form together with the nitrogen atom a 3–7 membered heterocyclic group, optionally substituted by a straight or branched $C_{1-4}$ alkyl group X stands for a —$CH_2$— group, —NH— group, —$NR^{11}$— group, or a sulphur atom or an oxygen atom or a sulpho group or a sulphoxy group—wherein $R^{11}$ stands for a straight or branched $C_{1-4}$ alkyl group or $C_{3-6}$ cycloalkyl group-;

n stands for zero, 1 or 2- m stands for 1, 2, 3 or 4, and o stands for zero, 1, 2, 3 or 4 and their salts, solvates, and their optically active isomers and the salts, solvates thereof fulfil the above criteria.

Detailed meanings of the above listed substituents are as follows:

By a straight or branched $C_{1-4}$ alkyl group we mean methyl-, ethyl-, propyl-, isopropyl-, butyl-, isobutyl-, secondary-butyl-, terciary-butyl-, preferably ethyl- or methyl group.

By a straight or branched $C_{1-4}$ alkoxy group we mean methoxy-, ethoxy-, propoxy-, isopropoxy-, butoxy-, isobutoxy-, secondary-butoxy-, terciary-butoxy-, preferably ethoxy- or methoxy group.

By a $C_{3-6}$ cycloalkyl group we mean cyclopropyl-, cyclobutyl-, cyclopentyl- or cyclohexyl group.

By a 3–7 membered heterocyclic ring we mean dimethyleneimine (aziridine), trimethyleneimine, tetramethyleneimine (pyrrolidine), pentemethylenimine (pyperidine) or hexamethyleneimine group.

The heteroaromatic ring containing one or two or three nitrogen atoms means pyrrol, imidazole, pyrazole, 1,2,3-triazole, 1,2,4-triazole, pyridine, pyrimidine, pyridazine, pyrazine and 1,3,4-triazine ring. The ring is optionally substituted by a $C_{1-4}$ alkyl, or alkoxy group or by a halogen atom.

The heteroaromatic ring containing one nitrogen atom and one oxygen or sulphur atom means oxazole, isoxazole, thiazole, isothiazole ring. The ring is optionally substituted by a $C_{1-4}$ alkyl, or alkoxy group or by a halogen atom.

Salts of the compounds of the general formula (I) mean salts given with inorganic and organic acids and bases. Preferred salts are those given with pharmaceutically accepted acids as for instance hydrochloric acid, sulphuric acid, ethanesulphonic acid, tartaric acid, succinic acid, fumaric acid, malic acid, citric acid, and bases, as for instance sodium hydroxide, potassium hydroxide, ethanolamine.

Solvates mean solvates given with various solvents, as for instance with water or ethanol.

The compounds of the general formula (I) show geometric and optical isomerism, therefore the invention also relates to mixtures of the geometric isomers, to racemic or optically active geometric isomers, as well as to their salts and solvates.

A favourable group of compounds of the general formula (I) is formed by the compounds wherein $R_1$ stands for hydrogen atom or a straight or branched $C_{1-4}$ alkyl group;

$R^2$ stands for hydrogen atom or a straight or branched $C_{1-4}$ alkyl group;

$R^3$ stands for hydrogen atom or a straight or branched $C_{1-4}$ alkyl group, or a $C_{3-6}$ cycloalkyl group or a phenyl group, thienyl group, or furyl group, optionally substituted by one or more straight or branched $C_{1-4}$ alkyl group, straight or branched $C_{1-4}$ alkoxy group, or halogen atom, or for a 5- or 6 membered heteroaromatic ring, containing one, two or three nitrogen atoms, or a 5 membered heteroaromatic ring, containing one nitrogen atom and one oxygen atom or one nitrogen atom and one sulphur atom, optionally substituted by one or more straight or branched $C_{1-4}$ alkyl group, straight or branched $C_{1-4}$ alkoxy group, or halogen atom;

$R^4$, $R^5$, $R^6$, and $R^7$ independently mean hydrogen atom or straight or branched $C_{1-4}$ alkyl group, or straight or branched $C_{1-4}$ alkoxy group, or hydroxy group or halogen atom, or $R^4$ and $R^7$ stand for hydrogen atom and $R^5$ and $R^6$ form together a methylenedioxy group;

$R^8$ stands for hydrogen atom or a cyano group, aminocarbonyl group, $C_{1-4}$ alkoxycarbonyl group, or carboxy group;

$R^9$ and $R^{10}$ stand independently from each other for hydrogen atom or a straight or branched $C_{1-4}$ alkyl group, or a $C_{3-6}$ cycloalkyl group, or a phenyl group, phenyl-$(C_{1-4})$ alkyl group, thienyl-$(C_{1-4})$alkyl group or furyl-$(C_{1-4})$alkyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for a —$(CH_2)_m$—OH or —$(CH_2)_o$—$NR^{12}R^{13}$ group, or $R^9$ and $R^{10}$ form together with the nitrogen atom a 3–7 membered heterocyclic group, optionally substituted by a straight or branched $C_{1-4}$ alkyl group;

$R^{12}$ and $R^{13}$ stand independently from each other for hydrogen atom or a straight or branched $C_{1-4}$ alkyl group, or a $C_{3-6}$ cycloalkyl group, or a phenyl group, phenyl-$(C_{1-4})$ alkyl group, thienyl-$(C_{1-4})$alkyl group or furyl-$(C_{1-4})$alkyl group, optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or for a —$(CH_2)_m$—OH or —$(CH_2)_o$—$NR^{12}R^{13}$ group, or $R^{12}$ and $R^{13}$ form together with the nitrogen atom a 3–7 membered heterocyclic group, optionally substituted by a straight or branched $C_{1-4}$ alkyl group X stands for a —$CH_2$— group, —NH— group, —$NR^{11}$— group, or a sulphur atom or an oxygen atom or a sulpho group or a sulphoxy group—wherein $R^{11}$ stands for a straight or branched $C_{1-4}$ alkyl group or $C_{3-6}$ cycloalkyl group;

n stands for zero, 1 or 2- m stands for 1, 2, 3 or 4, and o stands for zero, 1, 2, 3 or 4 and their salts, solvates, and optically active isomers and the salts, solvates thereof.

Another favourable group of compounds of the general formula is formed by the compounds wherein
$R^1$ stands for hydrogen atom, or methyl group;
$R^2$ stands for hydrogen atom, or methyl group;
$R^3$ stands for phenyl- or thienyl- or furyl group;
$R^4$, $R^5$, $R^6$, and $R^7$ mean independently hydrogen atom or straight or branched $C_{1-4}$ alkyl group, or straight or branched $C_{1-4}$ alkoxy group, or hydroxy group or halogen atom, or
$R^4$ and $R^7$ stand for hydrogen atom and $R^5$ and $R^6$ form together a methylenedioxy group;
$R^8$ stands for hydrogen atom, or cyano group;
$R^9$ and $R^{10}$ stand for methyl group, ethyl group or cyclopropyl group or $R^9$ and $R^{10}$ together with the nitrogen atom form a 3–7 membered heterocyclic group, optionally substituted by a straight or branched $C_{1-4}$ alkyl group,
X stands for —NH-group or for oxygen atom and
n stands for 1- and their salts, solvates, optically active isomers and the salts, solvates thereof.

Especially favourable are the following compounds complying with the above criteria:

1-(9-benzylamino-10-cyano-imidazo[1,2-a]quinolin-2-carbonyl)pyrrolidine;
N,N-dimethyl-9-benzylamino-10-cyano-imidazo[1,2-a]quinolin-2-carboxamide-hemihydrate;
N-ethyl-9-benzylamino-10-cyano-imidazo[1,2-a]quinolin-2-carboxamide-hemihydrate;
1-(9-furfurylamino-10-cyano-imidazo[1,2-a]quinolin-2-carbonyl)-pyrrolidine-hemihydrate;
1-(9-thienylamino-10-cyano-imidazo[1,2-a]quinolin-2-carbonyl)-pyrrolidine-hemihydrate;

and their salts, solvates, optically active isomers and the salts, solvates thereof.

According to another of its aspects, the present invention also relates to pharmaceutical compositions containing as active principles the compounds of the general formula (I) or their isomers, salts and solvates, which are preferably oral compositions, but inhalable, parenteral and transdermal formulations are also subjects of the invention. The above pharmaceutical compositions may be solids or liquides, such as tablets, pellets, capsules, patches, solutions, suspensions or emulsions. The solid compositions, first of all tablets and capsules are the preferred pharmaceutical forms.

The above pharmaceutical compositions are prepared by applying usual pharmaceutical excipients and by using standard methods.

The compounds of the general formula (I) can be used in treating pathologies, in the development of which $A_3$ receptor plays a role.

The compounds of the present invention having selective activity on the $A_3$ receptor can be used in the therapeutic and/or preventive treatment of disfunctions of the heart, kidney, respiratory system, central nervous system. They inhibit the protective effect of adenosine in growing tumor cells, prevent mast cell degranulation, inhibit the cytokine production, reduce the inraocular pressure, inhibit the TNFα release, inhibit the migration of eosinophils, neutrophils and other immune cells, inhibit the bronchoconstriction and plasma extravasation.

Based on these effects, adenosine $A_3$ receptor antagonists of the present invention may be therapeutically useful as antiinflammatory, antiasthmatic, antiischemic, antidepressant, antiarrhytmic, renal protective, antitumor, antiparkinson and cognitive enhancing drugs. They also may be useful in the treatment or prevention of miocardial reperfusion injury, chronic obstructive pulmonary disease (COPD) and adult respiratory distress syndrome (ARDS) including chronic bronchitis, pulmonary emphysema or dyspnea, allergic reactions (e.g. rhinitis, poison ivy induced responses, urticaria, scleroderma, arthritis) other autoimmune diseases, inflammatory bowel disease, Addison's disease, Crohn's disease, psoriasis, rheumatism, hypertension, neurogical function disorders, glaucoma and diabetes (K. N. Klotz, Naunyn-Schmiedberg's Arch. Pharmacol. 362:382, 2000; P. G. Baraldi és P. A. Borea, TiPS 21:456, 2000).

The compounds of the present invention may be preferable used for the treatment of diseases such as asthma, COPD and ARDS, glaucoma, tumor, allergic and inflammatory diseases, ischemia, hypoxia, arrythmia and renal diseases.

According to another of its aspects, the present invention relates to the use of the compounds of the general formula (I) in the treatment of the above pathologies. Suggested daily dose is 0,1–1000 mg active ingredient depending on the nature and severeness of the disease and on sex, weight etc. of the patient.

Further subject of the invention is the preparation of the compounds of the general formula (I) and of the intermediates of the general formulae (II) and (III).

The intermediates of the general formulae (II) and (III) which are used in the preparation process according to the invention, are partly novel. Substituents of the general formulae (II), (III), (IV) and (V) have the meanings as defined above.

Figure 1:
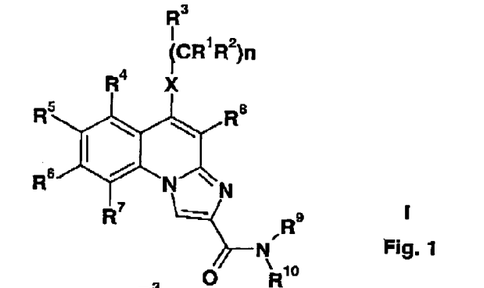
FIG. 1 shows compounds of formula (I)
Figure 2:
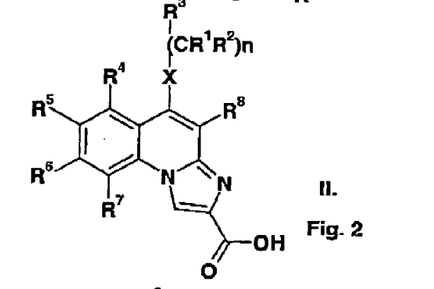
FIG. 2 shows compounds of formula (II)
Figure 8:
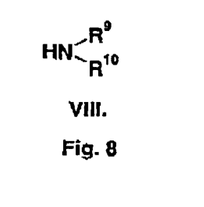
FIG. 8 shows compounds of formula (VIII).

In the process according to our invention a compound of the formula (VIII) is acylated with an acid of the general Formula (II), or a reactive derivative thereof according to the acylation reactions known in the organic chemistry. As acylating agents acid halogenides or mixed anhydrides are used and the compound of the general formula (I) thus obtained is, if desired, transformed into its salts, solvates or, liberated from its salt, solvate and separated into its geometric or optical isomers.

Substituents of the compounds of the general formula (I) may be transformed into each other by known methods.

The preparation of the mixed anhydride used in the acylation reaction is carried out with pivaloyl-chloride, preferable in the presence of an organic base, preferably triethylamine in chloroform, although other methods know form the organic chemistry can also be used. The acylation can be carried out within a wide temperature range, preferably between 0° C.–100° C.

Figure 3:
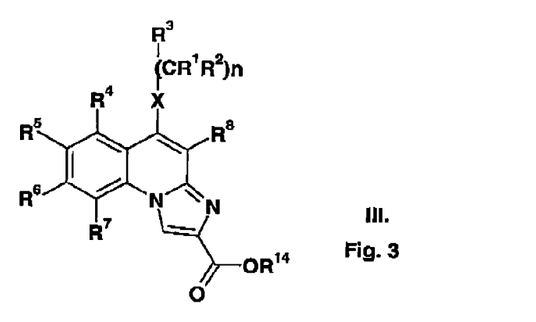
FIG. 3 shows compounds of formula (III)

The compounds of the general formula (II)—wherein the meanings of $R^1$, $R^2$, $R^3$, $R^4$, $R^5$, $R^6$, $R^7$, $R^8$, X and n are as defined above—can be obtained by several known methods, among them the one demonstrated in Scheme 1., by selective hydrolysis of the compounds of the formula (III), by using selective hydrolysing processes known in the organic chemistry. For hydrolysing agent preferably alkali hydroxides can be applied, but other agents helping the hydrolysis of esters can also be used.

Figure 4:
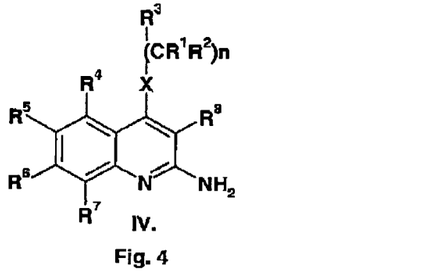
FIG. 4 shows compounds of formula (IV)

The compounds of the general formula (III)—wherein the meanings of $R^1$, $R^2$, $R^3$, $R^4$, $R^5$, $R^6$, $R^7$, $R^8$, X and n are as defined above and $R^{14}$ stands for $C_{1-4}$ alkyl group—can be prepared from the compounds of the formula (IV)—by using methods known per se (I. R. Ager and R. Westwood, J. Med. Chem. 31, 1098, (1988)).

Figure 5:
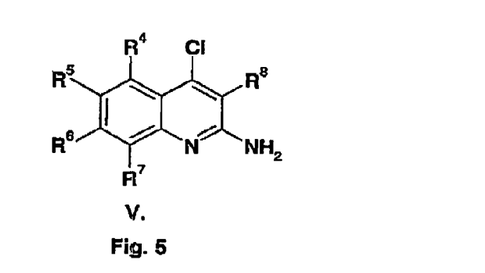
FIG. 5 shows compounds of formula (V)

The compounds of the general formula (IV)—wherein the meanings of $R^1$, $R^2$, $R^3$, $R^4$, $R^5$, $R^6$, $R^7$, $R^8$ and X and n are as defined above—can be prepared from the compounds of the formula (V), by using methods known per se (Nan Zhang, Bioorg. and Med. Chem. Lett., 10, 2825, (2000)).

Figure 6:
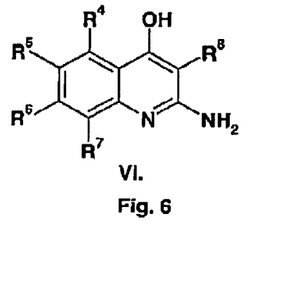
FIG. 6 shows compounds of formula (VI)
Figure 7:
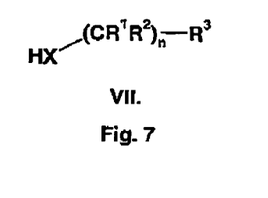
FIG. 7 shows compounds of formula (VII)

The compounds of the general formula (V)—wherein the meanings of $R^4$, $R^5$, $R^6$, $R^7$ and $R^8$ are as defined above—can be prepared from the compounds of the formula (VI), by using methods known per se (D. L. Leysen, J. Heterocyclic Chem., 24, 1611, (1987)).

The compounds of the general formula (VI)—wherein the meanings of $R^4$, $R^5$, $R^6$, $R^7$ and $R^8$ are as defined above—can be prepared by using methods known per se (Pfizer (Inc) U.S. Pat. No. 4,175,193).

The compounds of the invention, of the general formulae (I), (II), (III), (IV) and (V), their preparation and biological activity are demonstrated in the following Examples, without limiting the scope of claims to the Examples.

EXAMPLES

Example 1

1-(9-Benzylamino-10-cyano-imidazo[1,2-a]quinolin-2-carbonyl)-pyrrolidine

In general formula (I) $R^1$ and $R^2$ stand for hydrogen atoms, $R^3$ for phenyl group, $R^4$, $R^5$, $R^6$ and $R^7$ stand for hydrogen atom, $R^9$ and $R^{10}$ form together a 1,3-butandiyl group, $R^8$ stands for cyano group, the meaning of X is —NH group n is 1.

a.) 2-Amino-3-cyano-4-chloroquinolin

The mixture of 10 g of 2-amino-3-cyano-4-hydroxyquinolin and 15 ml of phosphoryl chloride is heated under stirring at 110° C. The reaction mixture is cooled down, poured onto 100 ml of ice-water and neutralized with 60 ml of 10% sodium hydroxide solution. The resulting yellow precipitate is filtered off, washed with 50 ml of water. After drying 7.5 g of the title compound is obtained, mp.: 210° C.

NMR, $\delta_H$ (400 MHz, DMSO-$d_6$): 7.21 ppm, (s, 2H, $NH_2$), 7.35–7.40 ppm, (dd, 1H, 6-H), 7.53–7.57 ppm, (d, 1H, 5-H), 7.70–7.75 ppm, (dd, 1H, 7-H), 7.93–7.98 ppm, (d, 1H, 8-H)

b.) 2-Amino-3-cyano-4-benzylaminoquinolin 5 g of 2-amino-3-cyano-4-chloroquinolin and 11 ml of benzylamine are heated under stirring at 130° C. The reaction mixture is poured onto 50 ml of water, the resulting precipitate is filtered off, washed with 50 ml of water. The pale-yellow precipitate is recrystallized from dimethylformamide to obtain 5.2 g of the title compound. Mp.: 206° C.

NMR, $\delta_H$ (400 MHz, DMSO-$d_6$): 5.02–5.03 ppm, (d, 2H, N—$CH_2$), 6.22 ppm, (s, 2H, $NH_2$), 7.14–7.16 ppm, (dd, 1H, 6-H), 7.24–7.26 ppm,(dd,1H, 5-H), 7.30 ppm, (s, 5H, Ph), 7.50–7.52 ppm, (dd, 1H, 7-H), 8.16–8.19 ppm, (d, 1H, 8-H), 8.30–8.33 ppm, (t, 1H, NH)

Using 2-aminomethylpyridine or 3-aminomethylpyridine or 4-aminomethylpyridine instead of benzylamine, the appropriate compounds of general formula IV can be obtained.

c.) Ethyl 9-benzylamino-10-cyano-imidazo[1,2-a]quinolin-2-carboxylate monohydrate To the solution of 2.74 g of 2-amino-3-cyano-4-benzylaminoquinolin in 100 ml of abs. ethanol 2.14 ml of ethyl bromopiruvate are added, under stirring at 70° C. The reaction mixture is boiled for 2 hour, than the precipitate is filtered off. The resulting white crystalline material is recrystallized from 150 ml of acetonitrile to give 1.1 g of the title compound, mp.: 112–114° C.

NMR, $\delta_H$ (400 MHz, DMSO-$d_6$): 1.32 ppm (t, 3H, COOCH$_2$CH$_3$), 4.30 ppm (q, 2H, COOCH$_2$CH$_3$), 5.09 ppm (d, 2H, PhCH$_2$), 7.25–7.38 ppm (m, 5H), 7.64–7.67 ppm (m, 1H),7.85–7.88 ppm (m, 1H), 8.43–8.53 ppm (m, 3H), 9.04 ppm (s, 1H, 3H).

d.) 9-Benzylamino-10-cyano-imidazo[1,2-a]quinolin-2-carboxylic acid

The mixture of 2.71 g. ethyl 9-benzylamino-10-cyano-imidazo[1,2-a]quinolin-2-carboxylate monohydrate, 42 ml ethanol and 40 ml of 10% sodium hydroxide solution is stirred for 6 hours on 25° C. To the thick suspension 100 ml water are added and the pH of the suspension is acidified to value 3 with a 96% acetic acid solution. The pale-yellow crystalline material is filtered off, washed with 3×25 ml water, and dried. Thus 2.3 g of the title compound are obtained Mp.:178–182° C.

NMR, $\delta_H$ (200 MHz, DMSO-$d_6$): 5.09 ppm (d, 2H, PhCH$_2$), 7.22–7.40 ppm (m, 5H), 7.59–7.67 ppm (m, 1H), 7.81–7.89 ppm (m, 1H), 8.37–8.54 ppm (m, 3H), 8.90 ppm (s, 1H, 3-H).

e. 1-(9-Benzylamino-10-cyano-imidazo[1,2-a]quinolin-2-carbonyl)-pyrrolidine To the mixture of 1.71 g. 9-benzylamino-10-cyano-imidazo[1,2-a]quinolin-2-carboxylic acid, 15 ml chloroform and 0.8 g triethylamin 0.6 g pivaloyl chloride in 10 ml chloroform are dropped, under stirring within 15 minutes at 5° C. The reaction mixture is stirred for 1 hour at 5° C., after that the mixture of 0.4 g pyrrolidine, 10 ml chloroform and 0,8 ml triethylamine is added to it. The mixture is stirred for 7 hours at 25°, diluted with 100 ml chloroform, extracted with 50 ml water, 50 ml of 5% sodium-hydrogen carbonate solution, and 50 ml water, dried on sodium-sulfate and evaporated in vacuo. The pale-yellow crystalline material is recrystallized from N,N-dimethylformamide to obtain 0.7 g of the title compound. Mp.: 206° C.

NMR, $\delta_H$ (400 MHz, DMSO-$d_6$): 1.79–1.92 ppm (m, 4H), 3.47–3.50 ppm (m, 2H), 3.95–3.98 ppm (m, 2H), 5.08 ppm (d, 2H, PhCH$_2$), 7.23–7.38 ppm (m, 5H), 7.62–7.65 ppm (m, 1H), 7.83–7.87 ppm (m, 1H), 8.36–8.42 ppm (m, 2H), 8.50–8.52 ppm (m, 1H), 8.80 ppm (s, 1H, 3-H).

Example 2

N,N-Dimethyl-9-benzylamino-10-cyano-imidazo[1,2-a]quinolin-2-carboxamide hemihydrate In the general formula (I) the meaning of $R^1$ and $R^2$ is hydrogen atom, $R^3$ is phenyl group, $R^4$, $R^5$, $R^6$ and $R^7$ stand for hydrogen, $R^8$ means cyano group, $R^9$ and $R^{10}$ mean independently from each other methyl group, X means —NH-group, n is 1.

To the mixture of 1.71 g. 9-benzylamino-10-cyano-imidazo[1,2-a]quinolin-2-carboxylic acid (prepared according to example 1), 15 ml chloroform and 0.8 g triethylamin 0.6 g pivaloyl chloride in 10 ml chloroform are dropped, under stirring within 15 minutes at 5° C. The reaction mixture is stirred for 1 hour at 9° C., than the mixture of 0.45 g dimethylammonium chloride, 10 ml chloroform and 1.6 ml triethylamine is added to it. The mixture is stirred for 3 hours at 25°, than the pale-yellow crystalline material obtained according to the procedure described in example 1 is recrystallized from N,N-dimethylformamide to obtain 0,65 g of the title compound. Mp.: 262–264° C.

NMR, $\delta_H$ (400 MHz, DMSO-$d_6$): 2.98 ppm (s, 3H), 3.45 ppm (s, 3H), 5.08 ppm (d, 2H, PhCH$_2$), 7.23–7.38 ppm (m, 5H), 7.62–7.65 ppm (m, 1H), 7.84–7.87 ppm (m, 1H), 8.37–8.39 ppm (m, 2H), 8.50–8.53 ppm (m, 1H), 8.75 ppm (s, 1H, 3-H).

Example 3

N-Ethyl-9-benzylamino-10-cyano-imidazo[1,2-a]quinolin-2-carboxamide hemihydrate In the general formula (I) the meaning of $R^1$ and $R^2$ is hydrogen atom, $R^3$ is phenyl group, $R^4$, $R^5$, $R^6$, and $R^7$ stand for hydrogen, $R^8$ means cyano group, $R^9$ means hydrogen, $R^{10}$ means ethyl group, X means —NH-group, n is 1.

1.71 g 9-benzylamino-10-cyano-imidazo[1,2-a]quinolin-2-carboxylic acid, prepared as described in Example 1., is transformed with 0.45 g ethylamine hydrochloride, analogously as described in previous Example ., into the title compound. After recrystallization of the pale-yellow material from 80 ml ethanol 0.62 g of the title compound, are obtained. Mp.:275–277° C.

NMR, $\delta_H$ (200 MHz, DMSO-$d_6$): 1.11 ppm (t, 3H, NHCH$_2$CH$_3$), 3.30 ppm (q, 2H, NHCH$_2$CH$_3$), 5.09 ppm (d, 2H, PhCH$_2$), 7.22–7.40 ppm (m, 5H), 7.60–7.67 ppm (m, 1H) 7.82–7.94 ppm (m, 2H), 8.38–8.42 ppm (m, 2H), 8,50–8,54 ppm (m, 1H), 8.82 ppm (s, 1H, 3-H).

Example 4

1-(9-Furfurylamino-10-cyano-imidazo[2-a]quinolin-2-carbonyl)-pyrrolidine hemihydrate In the general formula (I) the meaning of $R^1$ and $R^2$ is hydrogen atom, $R^3$ is 2-furyl group, $R^4$, $R^5$, $R^6$ and $R^7$ mean hydrogen, $R^9$ and $R^{10}$ mean together a 1,4-butandiyl group, $R^8$ means cyano group, means X means —NH-group, n is 1.

a) 2-Amino-3-cyano-furfurylaminoquinolin 10 g of 2-amino-3-cyano-4-chloroquinolin and 19 ml of furfurylamine are heated under stirring at 120° C., for 3 hours. The reaction mixture is cooled to 25° C., and six times successively mixed with 50 ml of water, the resulting precipitate is filtered off and dried. The material thus obtained is recrystallized from 60 ml dimethylformamide to obtain 5.8 g of the title compound. Mp.: 206° C.

NMR, $\delta_H$ (200 MHz, DMSO-$d_6$): 4.98 ppm (d, 2H, Furil-CH$_2$), 6.29 ppm (s, 2H), 6.35–6.42 ppm (m, 2H), 7.10–7.18 ppm (m, 1H), 7.31–7.35 ppm (m, 1H), 7.47–7.60 ppm (m, 2H), 8.13–8.20 ppm (m, 2H).

b) Ethyl 9-furfurylamino-10-cyano-imidazo[1,2-a]quinolin-carboxylate monohydrate To the solution of 2.64 g of 2-amino-3-cyano-4-furfurylaminoquinolin in 100 ml of abs. ethanol 2.14 ml of ethyl bromopiruvate are added, under stirring at 70° C. The reaction mixture is boiled for 2 hour, then the precipitate is filtered off, material is recrystallized 1,1 g of the title compound are obtained, mp.: 242–245° C.

NMR, $\delta_H$ (200 MHz, DMSO-$d_6$): 1,33 ppm (t, 3H, COOCH$_2$CH$_3$), 4.31 ppm (q, 2H, COOCH$_2$CH$_3$), 5.05 ppm (d, 2H, Furil-CH$_2$), 6.40–6.43 ppm (m, 2H), 7.58–7.66 ppm (m, 2H), 7.80–7.88 ppm (m, 1H), 8.31 ppm (t, 1H), 8.41–8.45 ppm (m, 2H) 9.04 ppm (s, 1H, 3-H).

c) 9-Furfurylamino-10-cyano-imidazo[1,2-a]quinolin-2-carboxylic acid

The mixture of 2.52 g. ethyl 9-furfurylamino-10-cyano-imidazo[1,2-a]quinolin-2-carboxylate monohydrate, 40 ml ethanol and 33 ml of 10% sodium hydroxide solution is stirred for 3 hours at 25° C. To the thick suspension 80 ml water are added and the pH of the suspension is acidified to value 3 with a 96% acetic acid solution. The pale-yellow crystalline material is filtered off, washed with 3×25 ml water, and dried. Thus 2.32 g of the title compound are obtained. Mp.:180–185° C., (decomposition).

NMR, $\delta_H$ (200 MHz, DMSO-$d_6$): 5.05 ppm (d, 2H, Furil-CH$_2$), 6.39–6.42 ppm (m, 2H), 7.56–7.64 ppm (m, 2H), 7.79–7.87 ppm (t, 1H), 8.27 ppm (m, 1H), 8.36–8.46 ppm (m, 2H), 8.93 ppm (s, 1H, 3-H).

d) 1-(9-Furfurylamino-10-cyano-imidazo[1,2-a]quinolin-2-carbonyl)-pyrrolidine hemihydrate To the mixture of 1.79 g. 9-furfurylamino-10-cyano-imidazo[1,2-a]quinolin-2-carboxylic acid, 15 ml chloroform and 0.8 g triethylaimin 0.6 g pivaloyl chloride in 10 ml chloroform are dropped, under stirring within 15 minutes at 5° C. The reaction mixture is stirred for 1 hour at 5° C., after that the mixture of 0,36 g pyrrolidine, 10 ml chloroform and 0.8 ml triethylamine is added to it. The mixture is stirred for 3 hours at 25°, diluted with 100 ml chloroform, extracted with 50 ml water, 50 ml of 5% sodium-hydrogen carbonate solution, and 50 ml water, dried on sodium-sulfate and evaporated in vacuo. The yellow crystalline material is recrystallized from 50 ml ethanol to obtain 0.15 g of the title compound. Mp.: 276–279° C.

NMR, $\delta_H$ (200 MHz, DMSO-$d_6$): 1.79–1.95 ppm (m, 4H), 3.47–3.54 ppm (m, 2H), 3.98–4.04 ppm (m, 2H), 5.05 ppm (d, 2H, Furil-CH$_2$), 6.40–6.44 ppm (m, 2H), 7.57–7.65 ppm (m, 2H), 7.80–7.88 ppm (m, 1H), 8.23 ppm (t, 1H), 8.39–8.46 ppm (m, 2H), 8.81 ppm (s, 1H, 3-H).

Example 5

1-(9-Thenylamino-10-cyano-imidazo[1,2-a]quinolin-2-carbonyl)-pyrrolidine hemihydrate In the general formula (I) the meaning of $R^1$ and $R^2$ is hydrogen atom, $R^3$ is 2-thienyl group, $R^4$, $R^5$, $R^6$ and $R^7$ mean hydrogen, $R^9$ and $R^{10}$ mean together a 1,4-butandiyl group, $R^8$ means cyano group, means X means —NH-group, n is 1.

a. 2-Amino-3-cyano-thenylaminoquinolin 10 g of 2-amino-3-cyano-4-chloroquinolin and 19 ml of thienylamine are heated under stirring at 115° C., for 4 hours. The reaction mixture is cooled to 25° C., and six times successively mixed with 50 ml of water, the resulting precipitate is filtered off, washed twice with 50 ml water and dried. The material thus obtained is recrystallized from 60 ml N,N-dimethylformamide to obtain 6.8 g pale-yellow title compound. Mp.: 208–209° C.

NMR, $\delta_H$ (200 MHz, DMSO-$d_6$): 5.18 ppm (d, 2H, Tienil-CH$_2$), 6.28 ppm (s, 2H), 6.96–7.00 ppm (m, 1H), 7.07–7.19 ppm (m, 2H), 7.31–7.42 ppm (m, 2H), 7.48–7.56 ppm (m, 1H), 8.09–8.13 ppm (m, 1H), 8.30 ppm (t, 1H).

b. Ethyl 9-thenylamino-10-cyano-imidazo[1,2-a]quinolin-carboxylate

To the solution of 5.61 g of 2-amino-3-cyano-4-thenylaminoquinolin in 200 ml of abs. ethanol 4.29 g of ethyl bromopiruvate are added, under stirring at 70° C. The reaction mixture is boiled for 2 hour, then the precipitate is filtered off. 2.54 g light beige title compound are obtained, mp.: 255–256° C.

NMR, $\delta_H$ (200 MHz, DMSO-$d_6$): 1.33 ppm (t, 3H, COOCH$_2$CH$_3$), 4.31 ppm (q, 2H, COOCH$_2$CH$_3$), 5.24 ppm (d, 2H, Tienil-CH$_2$), 6.96–7.00 ppm (m, 1H), 7.14 ppm (m, 1H), 7.40–7.43 ppm (m, 1H), 7.61–7.68 ppm (m, 1H), 7.82–7.90 ppm (m, 1H), 8.42–8.46 ppm (m, 3H), 9.05 ppm (s, 1H, 3-H).

c 9-Thenylamino-10-cyano-imidazo[1,2-a]quinolin-2-carboxylic acid

The mixture of 2.54 g. ethyl 9-thenylamino-10-cyano-imidazo[1,2-a]quinolin-2-carboxylate, 40 ml ethanol and 33 ml of 10% sodium hydroxide solution is stirred for 6 hours at 25° C. To the thick suspension 80 ml water are added and the pH of the suspension is acidified to value 3 with a 96% acetic acid solution.

The pale-yellow crystalline material is filtered off, washed with 5×10 ml water, and dried. Thus 2.18 g of the title compound are obtained. Mp.:209–217° C. (decomposition).

NMR, $\delta_H$ (400 MHz, DMSO-$d_6$): 5.24 ppm (d, 2H, Tienil-CH$_2$), 8.88 ppm (s, 1H, 3-H).

d. 1-(9-Thenylamino-10-cyano-imidazo[1,2-a]quinolin-2-carbonyl)-pyrrolidine hemihydrate To the mixture of 1.80 g. 9-thenylamino-10-cyano-imidazo[1,2-a]quinolin-2-carboxylic acid, 10 ml chloroform and 1,1 ml triethylamin 0.87 g pivaloyl chloride in 10 ml chloroform are dropped, under stirring within 15 minutes at 5° C. The reaction mixture is stirred for 1 hour at 5° C., after that the mixture of 0.51 g pyrrolidine, 10 ml chloroform and 1.1 ml triethylamine is added to it. The mixture is stirred for 3 hours at 25°, diluted with 100 ml chloroform, extracted with 50 ml water, 50 ml of 5% sodium-hydrogen carbonate solution, and 50 ml water, dried on sodium-sulfate and evaporated in vacuo. The yellow crystalline material is recrystallized from 200 ml ethanol to obtain 0.29 g of the title compound. Mp.: 267–269° C.

NMR, $\delta_H$ (400 MHz, DMSO-$d_6$): 1.79–1.94 ppm (m, 4H), 3.48–3.51 ppm (m, 2H), 3.98–4.01 ppm (m, 2H), 5.24 ppm (d, 2H, Tienil-CH$_2$), 6.97–7.00 ppm (m, 1H), 7.14 ppm (m, 1H), 7.41 ppm (m, 1H), 7.61–7.65 ppm (m, 1H), 7.83–7.87 ppm (m, 1H), 8.37–8.45 ppm (m, 3H), 8.82 ppm (s, 1H, 3-H).

Structure and physical characteristics of further compounds of general formula (I) prepared by the method described in Example 1. are shown in Table I.

TABLE I (I)

| No.: | X | $R^3$ | $R^9$ | $R^{10}$ | Mp [° C.] |
|---|---|---|---|---|---|
| 6. | NH | phenyl | H | propyl-N(Me)Me | 210 |
| 7. | NH | phenyl | H | CH(Me)-phenyl | 122 |
| 8. | NH | phenyl | H | CH(Me)-phenyl | 104 |
| 9. | NH | phenyl | H | ethyl-(3,4-diOMe-phenyl) | 185 |
| 10. | NH | phenyl | H | H | 265 |
| 11. | NH | phenyl | H | CH(Me)Me | 269 |
| 12. | NH | phenyl | H | CH$_2$-furyl | 248 |
| 13. | NH | phenyl | H | CH$_2$-cyclopentyl | 275 |
| 14. | NH | phenyl | H | CH$_2$-thienyl | 239 |
| 15. | NH | phenyl | H | CH$_2$CH$_2$OH | 149 |

TABLE I-continued (I)

[Structure: quinoline-imidazole fused ring system with X-CH(R³)(H) substituent, CN group, and C(=O)-N(R⁹)(R¹⁰) amide group]

| No.: | X | R³ | R⁹ | R¹⁰ | Mp [° C.] |
|---|---|---|---|---|---|
| 16. | NH | phenyl | H | cyclopropyl | 235 |
| 17. | NH | phenyl | H | Me | 280 |
| 18. | NH | phenyl | H | benzyl | 210 |
| 19. | NH | phenyl | H | 4-methoxybenzyl | 233 |
| 20. | NH | phenyl | H | 4-methoxy-3-methylphenyl | 234 |
| 21. | NH | phenyl | H | cyclohexyl-Me | 239 |
| 22. | O | Me | | cyclopentyl | 270 |
| 23. | O | phenyl | | cyclopentyl | 233 |
| 24. | S | phenyl | | cyclopentyl | 250 |
| 25. | S=O | phenyl | | cyclopentyl | 333 |
| 26. | SO₂ | phenyl | | cyclopentyl | 296 |

Structure and physical characteristics of the intermediates of the general formula (III) prepared by the method described in Example 1. are shown in Table (II)

TABLE II (III)

[Structure: quinoline-imidazole fused ring system with X-(CR¹R²)ₙ-R³ substituent, CN group, and C(=O)OC₂H₅ ester group]

| | R¹ | R² | R³ | X | n | Mp [° C.] |
|---|---|---|---|---|---|---|
| 27. | Me (wedge) | H | phenyl | NH | 1 | 146 |
| 28. | Me (dash) | H | phenyl | NH | 1 | 145 |
| 29. | H | H | 2,4-dimethoxyphenyl | NH | 2 | 34 |
| 30. | H | H | phenyl | NH | 2 | 32 |

TABLE II-continued

Structure III: quinoline-imidazole fused system with X-(CR¹R²)ₙ-R³ substituent, CN group, and -C(=O)OC₂H₅ group.

| No. | R¹ | R² | R³ | X | n | Mp [° C.] |
|---|---|---|---|---|---|---|
| 31. | | | cyclohexyl | NH | 0 | 250 |
| 32. | | | cyclopentyl | NH | 0 | 128 |
| 33. | H | H | 4-MeO-phenyl | NH | 1 | 45 |
| 34. | H | H | 2-MeO-phenyl | NH | 1 | 54 |
| 35. | H | H | phenyl | O | 1 | 185 |
| 36. | H | H | phenyl | S | 1 | 190 |
| 37. | H | H | pyridyl | S=O | 1 | 230 |
| 38. | H | H | phenyl | O=S=O | 1 | 255 |

Structure and physical characteristics of the intermediates of the general formula (IV) prepared by the method described in Example 1. are shown in Table (III)

TABLE III

Structure (IV): 2-amino-3-cyano-quinoline with R⁵, R⁶ substituents and X-(CR¹R²)ₙ-R³ at position 4.

| No.: | R¹ | R² | R³ | R⁵ | R⁶ | X | n | Mp [° C.] |
|---|---|---|---|---|---|---|---|---|
| 39. | H | H | 2-OMe-phenyl | H | H | NH | 1 | 192 |
| 40. | H | H | 4-OMe-phenyl | H | H | NH | 1 | 202 |
| 41. | H | H | 2-Cl-phenyl | H | H | NH | 1 | 250 |
| 42. | H | H | 3-Cl-phenyl | H | H | NH | 1 | 167 |
| 43. | H | ⫶Me | phenyl | H | H | NH | 1 | 183 |
| 44. | H | ▲Me | phenyl | H | H | NH | 1 | 182 |
| 45. | H | H | phenyl | H | H | NH | 2 | 172 |
| 46. | H | H | 3,4-di-OMe-phenyl | H | H | NH | 2 | 143 |
| 47. | H | ⫶Me | phenyl | H | H | NH | 2 | 129 |
| 48. | H | ▲Me | phenyl | H | H | NH | 2 | 136 |
| 49. | H | H | phenyl | H | H | N-Me | 1 | 212 |

TABLE III-continued (IV)

| No.: | R¹ | R² | R³ | R⁵ | R⁶ | X | n | Mp [° C.] |
|---|---|---|---|---|---|---|---|---|
| 50. | H | H | phenyl | H | H | S | 1 | 168 |
| 51. | H | H | phenyl | H | H | O | 1 | 213 |
| 52. | H | H | phenyl | Cl | H | NH | 1 | 234 |
| 53. | H | H | furyl | Cl | H | NH | 1 | 221 |
| 54. | H | H | phenyl | Me | H | NH | 1 | 198 |
| 55. | H | H | phenyl | MeO | H | NH | 1 | 201 |
| 56. | H | H | phenyl | H | Cl | NH | 1 | 191 |
| 57. | H | H | phenyl | OH | H | NH | 1 | 246 |
| 58. | H | H | 3-iodophenyl | H | H | NH | 1 | 227 |
| 59. | H | H | thienyl | MeO | H | NH | 1 | 217 |
| 60. | H | H | thienyl | Me | H | NH | 1 | 198 |
| 61. | H | H | thienyl | Cl | H | NH | 1 | 168 |
| 62. | | | phenyl | H | H | NH | 0 | 214 |

Structure and physical characteristics of the intermediates of the general formula (V) prepared by the method described in Example 1. are shown in Table (IV)

TABLE IV

| No: | R⁴ | R⁵ | R⁶ | R⁷ | Mp[° C.] |
|---|---|---|---|---|---|
| 63. | H | OH | H | H | 360 |
| 64. | H | Cl | H | H | 250 |
| 65. | H | H | Cl | H | 278 |
| 66 | H | Me | H | H | 283 |
| 67. | H | OMe | H | H | 360 |
| 68. | H | H | H | OMe | 234 |
| 69 | Me | H | H | H | 246 |
| 70 | H | H | H | Me | 267 |
| 71 | H | I | H | H | 293 |

Example 72

Tablets of the following composition are made by known methods used in the pharmaceutical industry

| | |
|---|---|
| Active ingredient | 25 mg |
| Lactose | 50 mg |
| Avicel | 21 mg |
| Crospovidone | 3 mg |
| Magnesium stearate | 1 mg |

Biology
Methods
Human Adenosine $A_3$ Receptor Binding
Preparing membrane suspension: collect CHO cells expressing hA3 receptors by washing three times with ice cold PBS, centrifugate at 100×g 10 min, homogenize for 15 sec in buffer (50 mM Tris, 10 mM $MgCl_2$, 1 mM EDTA, pH 8.0), centrifugate at 43.000×g for 10 min (Sigma 3K30), suspense the membrane preparation in the buffer mentioned above, store the aliquots at −80 C.

Binding protocol: incubate CHO-hA$_3$ membrane preparation (2 μg protein content) in incubation buffer (50 mM Tris, 10 mM MgCl$_2$, 1 mM EDTA, 3 U/mL adenosine deaminase, pH 8.0), in the presence of 0.5 nM [$^{125}$I]AB-MECA (p-amino-benzyl-methylcarboxamido-adenosine) (100.000 cpm) and 100 μM R-PIA (N$^6$-[L-2-phenylisopropyl]adenosine) to define non-specific binding or test compound in a total volume of 50 μL for 1 hr at room temperature. Filter over Whatman GF/B glass fibre filters (presoaked in 0.5% polyethylenimine for 3 hours), wash 4× with 1 mL ice-cold 50 nm Tris, 10 mM MgCl$_2$, 1 mM EDTA (pH 8.0) on 96-well Brandel Cell Harvester. Detection of activity: in gamma-counter (1470 Wizard, Wallac). Inhibition [%]=100−((activity in the presence of test compound−non-specific activity)/(total activity−non-specific activity))*100

Human Adenosine A$_1$ Receptor Binding

Preparing membrane suspension: collect CHO cells expressing hA$_1$ receptors by washing three times with ice cold PBS, centrifugate at 1000×g 10 min, homogenize for 15 sec in buffer (50 mM Tris, pH 7.4), centrifugate at 43.000×g for 10 min (Sigma 3K30), suspense the membrane preparation in the buffer mentioned above, store the aliquots at −80 C.

Binding protocol: incubate CHO-hA$_1$ membrane preparation (50 μg protein content) in incubation buffer (50 mM Tris, 3 U/mL adenosine deaminase, pH 7.4), 10 nM [$^3$H] CCPA (2-chloro-N$^6$-cyclopenthyl-adenosine) (80.000 dpm) and 10 μM R-PIA (N$^6$-[L-2-phenylisopropyl]adenosine) to define the non-specific binding or test compound in a total volume of 100 μL for 3 hr at room temperature. Filter over Whatman GF/B glass fibre filters (presoaked in 0.5% polyethylenimine for 3 hours), wash 4× with 1 mL ice-cold 50 mM Tris (pH 7.4) on 96-well Brandel Cell Harvester. Detection of activity: in 96-well plate in the presence of HiSafe-3 coctail in beta-counter (1450 Microbeta, Wallac). Inhibition [%]=100−((activity in the presence of test compound−non-specific activity)/(total activity−non-specific activity))*100

Human Adenosine A$_{2a}$ Receptor Binding

Binding protocol: incubate 7 μg of membranes (human A$_{2a}$ adenosine receptors transfected into HEK-293 cells, source: Receptor Biology, Inc.), buffer (50 mM Tris-HCl, 10 mM MgCl$_2$, 1 mM EDTA, 2 U/mL adenosine deaminase, pH 7.4), 20 nM [$^3$H]CGS-21680 (2-[p-(2-carbonylethyl)phenylethylamino]-5'-N-ethylcarboxamido-adenosine) (200.000 dpm) and 50 μM NECA (5'-N-ethylcarboxamido-adenosine) to define the non-specific binding or test compound in a total volume of 100 μl for 90 min at room temperature. Filter over Whatman GF/B glass fibre filters (presoaked in 0.5% polyethylenimine), wash 4× with 1 mL ice-cold 50 mM Tris, 10 mM MgCl$_2$, 1 mM EDTA, 0.9 % NaCl, pH 7.4) on 96-well Brandel Cell Harvester. Detection of activity: in 96-well plate in the presence of HiSafe-3 coctail in beta-counter (1450 Microbeta, Wallac). Inhibition [%]100−((activity in the presence of test compound−non-specific activity)/(total activity−non-specific activity))*100

Human Adenosine A$_{2b}$ Receptor Binding

Binding protocol: incubate 20.8 μg of membranes (human A$_{2b}$ adenosine receptors transfected into HEK-293 cells, source: Receptor Biology, Inc.), buffer (50 mM Tris-HCl, 10 mM MgCl$_2$, 1 mM EDTA, 0.1 mM benzamidine, 2 U/mL adenosine deaminase, pH 6.5), 32.4 nM [$^3$H]DPCPX (8-cyclopenthyl-1,3-dipropylxanthine) (800.000 dpm) and 100 μM NECA (5'-N-ethylcarboxamido-adenosine) to define non-specific binding or test compound in a total volume of 100 μL for 30 min at room temperature. Filter over Whatman GF/C glass fibre filters (presoaked in 0.5% polyethylenimine), wash 4× with 1 mL ice-50 mM Tris-HCl (pH 6.5) on 96-well Brandel Cell Harvester. Detection of activity: in 96-well plate in the presence of HiSafe-3 coctail in beta-counter (1450 Microbeta, Wallac). Inhibition [%]100−((activity in the presence of test compound−non-specific activity)/(total activity−non-specific activity))*100

Results

We consider the compounds as biologically active ones if they inhibit the binding of the radioligand on human adenosine A$_3$ receptors with an activity above 80% at 1 μM in our experimental conditions.

The dissociation constant (K$_d$) of [$^{125}$I]-MECA on CHO-hA$_3$ membrane preparation is determined by isotope saturation studies with the help of Seatchard analysis (G. Scatchard, Ann. N. Y. Acad. Sci. 51:660, 1949). The IC$_{50}$ is converted to an affinity constant (K$_i$) by application of the Cheng-Prusoff equation (Y. J. Cheng and W. H. Prusoff, Biochem. Pharmacol. 22:3099, 1973).

Several compounds of the general formula (I), (II), (III) and (IV) display remarkable biological effects. The compounds of the general formula (I), defined in claim 2, as a subgroup of the general formula (I), defined in claim 1, exert the most important activities. Except of 9 compounds, their K$_i$ values are nor higher than 150 nM. The compounds given as examples are especially advantageous. Their K$_i$ values in human adenosine A$_3$ receptor binding studies are between 1.6 and 0.38 nM. The K$_i$ values of the most advantageous compounds are 0.52 and 0.38 nM.

The compounds possess proper bioviabilities and exert at least 1,000-fold selectivity in respect of human adenosine A$_1$, A$_{2a}$, and A$_{2b}$ receptor subtypes.

Further, the duration of their action at intravenous and oral administration is long enough, their ED$_{50}$ values are low, their toxicological and side-effect profiles are advantageous.

Data above make the compounds of the general formula (I) probable for therapeutic applications.

The invention claimed is:

1. A compound of formula (I)

wherein
R$^1$ is hydrogen atom or a straight or branched C$_{1-4}$ alkyl group;
R$^2$ is hydrogen atom or a straight or branched C$_{1-4}$ alkyl group;
R$^3$ is hydrogen atom, a straight or branched C$_{1-4}$ alkyl group, C$_{3-6}$ cycloalkyl group,
a phenyl group, thienyl group, or furyl group, each of which is optionally substituted by one or more straight or branched C$_{1-4}$ alkyl group, straight or branched C$_{1-4}$ alkoxy group, or halogen atom, or
a 5 or 6 membered heteroaromatic ring, containing one, two or three nitrogen atoms, or a 5 membered heteroaromatic ring, containing one nitrogen atom and one oxygen atom or one nitrogen atom and one sulphur atom, each of which is optionally substituted by one or more straight or branched $C_{1-4}$ alkyl group, straight or branched $C_{1-4}$ alkoxy group, or halogen atom;

$R^4$, $R^5$, $R^6$ and $R^7$ are independently from each other hydrogen atom, a straight or branched $C_{1-4}$ alkyl group, straight or branched $C_{1-4}$ alkoxy group, hydroxy group or halogen atom, or $R^4$ and $R^7$ are hydrogen atom, and $R^5$ and $R^6$ form together a methylenedioxy group;

$R^8$ is hydrogen atom, a cyano group, aminocarbonyl group, $C_{1-4}$ alkoxycarbonyl group, or carboxy group;

$R^9$ and $R^{10}$ are independently from each other hydrogen atom, a straight or branched $C_{1-4}$ alkyl group, a $C_{3-6}$ cycloalkyl group, a phenyl group, phenyl-straight or branched $(C_{1-4})$alkyl group, thienyl-straight or branched $(C_{1-4})$alkyl group or furyl-straight or branched $(C_{1-4})$alkyl group, wherein phenyl, thienyl or furyl moiety of the phenyl group, phenyl-straight or branched $(C_{1-4})$alkyl group, thienyl-straight or branched $(C_{1-4})$alkyl group or furyl-straight or branched $(C_{1-4})$alkyl group is optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, a 5 or 6 membered heteroaromatic ring, containing one, two or three nitrogen atoms, or a 5 membered heteroaromatic ring, containing one nitrogen atom and one oxygen atom or one nitrogen atom and one sulphur atom, each of which is optionally substituted by one or more straight or branched $C_{1-4}$ alkyl group, straight or branched $C_{1-4}$ alkoxy group, or halogen atom, or a —$(CH_2)_m$—OH or —$(CH_2)_o$—$NR^{12}R^{13}$ group, or $R^9$ and $R^{10}$ taken together with the nitrogen atom to which they are attached form a 3–7 membered heterocyclic group containing only one heteroatom, optionally substituted by a straight or branched $C_{1-4}$ alkyl group;

$R^{12}$ and $R^{13}$ are independently from each other hydrogen atom, a straight or branched $C_{1-4}$ alkyl group, a $C_{3-6}$ cycloalkyl group, a phenyl group, phenyl-straight or branched $(C_{1-4})$alkyl group, thienyl-straight or branched $(C_{1-4})$alkyl group or furyl-straight or branched $(C_{1-4})$alkyl group, wherein phenyl, thienyl or furyl moiety of the phenyl group, phenyl-straight or branched $(C_{1-4})$alkyl group, thienyl-straight or branched $(C_{1-4})$alkyl group or furyl-straight or branched $(C_{1-4})$alkyl group is optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, a 5 or 6 membered heteroaromatic ring, containing one, two or three nitrogen atoms, or a 5 membered heteroaromatic ring, containing one nitrogen atom and one oxygen atom or one nitrogen atom and one sulphur atom, each of which is optionally substituted by one or more straight or branched $C_{1-4}$ alkyl group, straight or branched $C_{1-4}$ alkoxy group, or halogen atom, or a —$(CH_2)_m$—OH or —$(CH_2)_o$—$NR^{12}R^{13}$ group, or $R^{12}$ and $R^{13}$ taken together with the nitrogen atom to which they are attached form a 3–7 membered heterocyclic group, optionally substituted by a straight or branched $C_{1-4}$ alkyl group, X is a —$CH_2$— group, —NH— group, —$NR^{11}$— group, a sulphur atom, an oxygen atom, a sulpho group or a sulphoxy group, wherein $R^{11}$ is a straight or branched $C_{1-4}$ alkyl group or $C_{3-6}$ cycloalkyl group;

n 0, 1 or 2;

m is 1, 2, 3 or 4; and o 0, 1, 2, 3 or 4;

or a salt, solvate, or optically active isomer thereof, or a salt or solvate of the optically active isomer.

2. The compound of formula (I) according to claim 1, wherein $R^9$ and $R^{10}$ are independently from each other hydrogen atom, a straight or branched $C_{1-4}$ alkyl group or $C_{3-6}$ cycloalkyl group;

a phenyl group, phenyl-straight or branched $(C_{1-4})$alkyl group, thienyl-straight or branched $(C_{1-4})$alkyl group or furyl-straight or branched $(C_{1-4})$alkyl group, wherein phenyl, thienyl or furyl moiety of the phenyl group, phenyl-straight or branched $(C_{1-4})$alkyl group, thienyl-straight or branched $(C_{1-4})$alkyl group or furyl-straight or branched $(C_{1-4})$alkyl group is optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or a —$(CH_2)_m$—OH or —$(CH_2)_o$—$NR^{12}R^{13}$ group, or $R^9$ and $R^{10}$ taken together with the nitrogen atom to which they are attached form a 3–7 membered heterocyclic group, optionally substituted by a straight or branched $C_{1-4}$ alkyl group; and $R^{12}$ and $R^{13}$ are independently from each other hydrogen atom, a straight or branched $C_{1-4}$ alkyl group, a $C_{3-6}$ cycloalkyl group, a phenyl group, phenyl-$(C_{1-4})$alkyl group, thienyl-$(C_{1-4})$alkyl group or furyl-$(C_{1-4})$alkyl group, wherein phenyl, thienyl or furyl moiety of the phenyl group, phenyl-$(C_{1-4})$alkyl group, thienyl-$(C_{1-4})$alkyl group or furyl-$(C_{1-4})$alkyl group is optionally substituted by a methylenedioxy group, or one or more straight or branched $C_{1-4}$ alkyl group, straight or branched $C_{1-4}$ alkoxy group, hydroxy group, trifluoromethyl group, cyano group or halogen atom, or a —$(CH_2)_m$—OH or —$(CH_2)_o$—$NR^{12}R^{13}$ group, or $R^{12}$ and $R^{13}$ taken together with the nitrogen atom to which they are attached form a 3–7 membered heterocyclic group, optionally substituted by a straight or branched $C_{1-4}$ alkyl group, or a salt, solvate, or optically active isomer thereof, or a salt or solvate of the optically active isomer.

3. The compound of formula (I) according to claim 1 wherein $R^1$ is hydrogen atom, or methyl group;

$R^2$ is hydrogen atom, or methyl group;

$R^3$ is phenyl, thienyl or furyl group;

$R^8$ is hydrogen atom, or cyano group;

$R^9$ and $R^{10}$ are independently methyl group, ethyl group or cyclopropyl group, or

$R^9$ and $R^{10}$ taken together with the nitrogen atom to which they are attached form a 3–7 membered heterocyclic group, optionally substituted by a straight or branched $C_{1-4}$ alkyl group;

X is —NH— group or oxygen atom; and n is 1;
or a salt, solvate, or optically active isomer thereof, or a salt or solvate of the optically active isomer.

4. The compound according to claim 1, which is:
1-(9-benzylamino-10-cyano-imidazo[1,2-a]quinolin-2-carbonyl)pyrrolidine;
N,N-dimethyl-9-benzylamino-10-cyano-imidazo[1,2-a]quinolin-2-carboxamide-hemihydrate;
N-ethyl-9-benzylamino-10-cyano-imidazo[1,2-a]quinolin-2-carboxamide-hemihydrate;
1-(9-furfurylamino-10-cyano-imidazo[2-a]quinolin-2-carbonyl)-pyrrolidine-hemihydrate; or
1-(9-thienylamino-10-cyano-imidazo[1,2-a]quinolin-2-carbonyl)-pyrrolidine-hemihydrate;
or a salt, solvate, or optically active isomer thereof, or a salt or solvate of the optically active isomer.

5. A process for the preparation of a compound Or formula (I),

(I)

a salt, solvate, or optically active isomer thereof, or a salt or solvate of the optically active isomer, wherein $R^1$, $R^2$, $R^3$, $R^4$, $R^5$, $R^6$, $R^7$, $R^8$, $R^9$, $R^{10}$, X, and n, have the same meaning as defined in claim 1, comprising acylating a compound of formula (VIII), (VIII)

wherein $R^9$ and $R^{10}$ have the same meaning as defined in claim 1, with an acid of formula (II), (II)

wherein $R^1$, $R^2$, $R^3$, $R^4$, $R^5$, $R^6$, $R^7$, $R^8$, X and n have the same meaning as defined in claim 1, or a reactive derivative of the acid of formula (II), to form the compound of formula (I) corresponding thereto,
wherein the reactive derivative is an acid halid or anhydride of the acid of formula (II).

6. The process according to claim 5 wherein the acylation is carried out in an organic solvent, and in the presence of a base.

7. The process according to claim 5 wherein the acylation is carried out in a halogenated hydrocarbon organic solvent.

8. The process according to claim 5 wherein the acylation is carried out in the presence of an organic base.

9. A pharmaceutical composition comprising one or more compounds according to claim 1 or a salt, solvate, or optically active isomer thereof, or a salt or solvate of the optically active isomer, in admixture with one or more excipients.

10. A pharmaceutical composition comprising one or more compounds of claim 3 or a salt, solvate, or optically active isomer thereof, or a salt or solvate of the optically active isomer, in admixture with one or more excipients.

11. A pharmaceutical composition comprising one or more compounds of claim 4 or a salt, solvate, or optically active isomer thereof, or a salt or solvate of the optically active isomer, in admixture with one or more excipients.

12. A method for treating asthma, an inflammatory disease, ischemia, arrhythmia or a renal disease, wherein receptor $A_3$ plays a role, in a patient in need thereof, comprising administering to the patient a pharmaceutically effective amount of a compound according to claim 1.

13. A compound of formula (II)

(II)

wherein $R^1$, $R^2$, $R^3$, $R^4$, $R^5$, $R^6$, $R^7$, $R^8$, X and n have the same meaning as defined in claim 1, provided that if —X—(CR$^1$R$^2$)$_n$—R$^3$ together form an alkoxy, alkylthio, alkylsulfo or alkylsulfoxy group, $R^8$ is not hydrogen.

14. A compound of formula (III)

(III)

wherein $R^1$, $R^2$, $R^3$, $R^4$, $R^5$, $R^6$, $R^7$, $R^8$, X and n have the same meaning as defined in claim 1, and $R^{14}$ is $C_{1-4}$ alkyl group, provided that if —X—$(CR^1R^2)_n$—$R^3$ together form an alkoxy or alkylthio group, $R^8$ is not hydrogen.

15. The compound of formula (I) according to claim 2 wherein
- $R^1$ is hydrogen atom, or methyl group;
- $R^2$ is hydrogen atom, or methyl group;
- $R^3$ is phenyl, thienyl or furyl group;
- $R^8$ stands for hydrogen atom, or cyano group;
- $R^9$ and $R^{10}$ are independently methyl group, ethyl group or cyclopropyl group, or
- $R^9$ and $R^{10}$ taken together with the nitrogen atom to which they are attached form a 3–7 membered heterocyclic group, optionally substituted by a straight or branched $C_{1-4}$ alkyl group;
- X is —NH— group or oxygen atom; and
- n is 1;
- or a salt, solvate, or optically active isomer thereof, or a salt or solvate of the optically active isomer.

16. The process according to claim 6 wherein the organic solvent is a halogenated hydrocarbon organic solvent.

17. The process according to claim 7 wherein the halogenated hydrocarbon organic solvent is chloroform.

18. The process according to claim 16, wherein the halogenated hydrocarbon organic solvent is chloroform.

19. The process according to claim 6 wherein the base is an organic base.

20. The process according to claim 7 wherein the acylation is carried out in the presence of an organic base.

21. The process according to claim 8 wherein the organic base is triethylamine.

22. The process according to claim 19 wherein the organic base is triethylamine.

23. The process according to claim 20 wherein the organic base is triethylamine.

24. A pharmaceutical composition comprising one or more compounds of claim 2 or a salt, solvate, or optically active isomer thereof, or a salt or solvate of the optically active isomer, in admixture with one or more excipients.

25. A pharmaceutical composition comprising one or more compounds of claim 15 or a salt, solvate, or optically active isomer thereof, or a salt or solvate of the optically active isomer, in admixture with one or more excipients.

* * * * *